United States Patent
Howe et al.

(10) Patent No.: US 6,670,379 B2
(45) Date of Patent: Dec. 30, 2003

(54) PIPERIDINE COMPOUNDS FOR USE AS CCR-3 INHIBITORS

(75) Inventors: Trevor John Howe, Horsham (GB); Gurdip Bhalay, Horsham (GB); Darren Mark Le Grand, Horsham (GB); Thomas Storz, Thousand Oaks, CA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 10/332,642

(22) PCT Filed: Jul. 10, 2001

(86) PCT No.: PCT/EP01/07941

§ 371 (c)(1),
(2), (4) Date: Apr. 17, 2003

(87) PCT Pub. No.: WO02/04420

PCT Pub. Date: Jan. 17, 2002

(65) Prior Publication Data

US 2003/0176460 A1 Sep. 18, 2003

(30) Foreign Application Priority Data

Jul. 12, 2000 (GB) ................................ 0017174
Sep. 22, 2000 (GB) ................................ 0023326

(51) Int. Cl.[7] ....................... A61F 31/445; C07D 211/32
(52) U.S. Cl. ....................... 514/330; 546/225; 546/214; 546/196; 514/326; 514/318
(58) Field of Search ................ 514/330, 326, 514/318; 546/225, 214, 196

(56) References Cited

U.S. PATENT DOCUMENTS

| | | | | |
|---|---|---|---|---|
| 6,140,344 A | * | 10/2000 | Gong et al. ........ | 514/317 |
| 6,323,223 B1 | | 11/2001 | Gong et al. ........ | 514/331 |
| 6,339,087 B1 | | 1/2002 | Gong et al. ........ | 514/252.12 |
| 6,518,286 B1 | * | 2/2003 | Baxter et al. ........ | 514/327 |

FOREIGN PATENT DOCUMENTS

| | | |
|---|---|---|
| GB | 2330580 | 4/1999 |
| GB | 2343891 | 5/2000 |
| WO | 99/04794 | 2/1999 |
| WO | 00/29377 | 5/2000 |
| WO | 00/35454 | 6/2000 |
| WO | 00/58305 | 10/2000 |

OTHER PUBLICATIONS

* Ponath, "Chemokine Receptor Antagonists: Novel Therapeutics for Inflammationand AIDS", Expert Opinion on Investigational Drugs, Ashley Publications Ltd., London, GB, vol. 7, No. 1, pp. 1–18 (1998).

* cited by examiner

Primary Examiner—C. S. Aulakh
(74) Attorney, Agent, or Firm—D. Gabrielle Brouillette; Susan L. Hess

(57) ABSTRACT

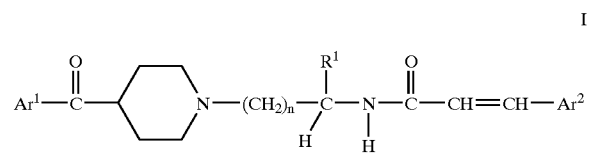

Compounds of formula (I) in free or salt form, where $Ar^1$ is phenyl substituted by one or more halogen atoms, $Ar^2$ is phenyl or naphthyl which is unsubstituted or substituted by one or more substituents selected from halogen, cyano, hydroxy, nitro, $C_1$–$C_8$-alkyl, $C_1$–$C_8$-haloalkyl, $C_1$–$C_8$-alkoxy or $C_1$–$C_8$-alkoxycarbonyl, $R^1$ is hydrogen or $C_1$–$C_8$-alkyl optionally substituted by hydroxy, $C_1$–$C_8$-alkoxy, acyloxy, $N(R^2)R^3$, halogen, carboxy, $C_1$–$C_8$-alkoxycarbonyl, —CON($R^4$)$R^5$ or by a monovalent cyclic organic group, $R^2$ and $R^3$ are each independently hydrogen or $C_1$–$C_8$-alkyl, or $R^2$ is hydrogen and $R^3$ is acyl or —$SO_2R^6$, or $R^2$ and $R^3$ together with the nitrogen atom to which they are attached denote a 5 or 6-membered heterocyclic group, $R^4$ and $R^5$ are each independently hydrogen or $C_1$–$C_8$-alkyl, or $R^4$ together with the nitrogen atom to which they are attached denote a 5 or 6-membered heterocyclic group, $R^6$ is $C_1$–$C_8$-alkyl, $C_1$–$C_8$-haloalkyl, or phenyl optionally substituted by $C_1$–$C_8$-alkyl, and n is 1, 2, 3, or 4, with the proviso that when $Ar^1$ is p-chlorophenyl and $R^1$ is hydrogen, $R^2$ is not phenyl or p-nitrophenyl. The compounds are useful as pharmaceuticals.

20 Claims, No Drawings

PIPERIDINE COMPOUNDS FOR USE AS CCR-3 INHIBITORS

This application is a 371 of PCT/EP01/07941 filed Jul. 10, 2001, now WO 02/04420 Jan. 17, 2002.

This invention relates to organic compounds, their preparation and their use as pharmaceuticals.

In one aspect, the invention provides compounds of formula

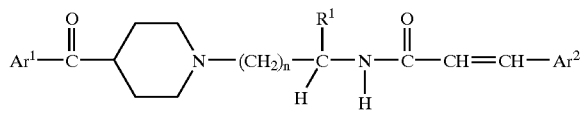

in free or salt form, where

Ar$^1$ is phenyl substituted by one or more halogen atoms,

Ar$^2$ is phenyl or naphthyl which is unsubstituted or substituted by one or more substituents selected from halogen, cyano, hydroxy, nitro, $C_1$–$C_8$-alkyl, $C_1$–C8-haloalkyl, $C_1$–$C_8$-alkoxy or $C_1$–$C_8$-alkoxycarbonyl, R$^1$ is hydrogen or $C_1$–$C_8$-alkyl optionally substituted by hydroxy, $C_1$–$C_8$-alkoxy, acyloxy, —N(R$^2$)R$^3$, halogen, carboxy, $C_1$–$C_8$-alkoxycarbonyl, —CON(R$^4$)R$^5$ or by a monovalent cyclic organic group, R$^2$ and R$^3$ are each independently hydrogen or $C_1$–$C_8$-alkyl, or R$^2$ is hydrogen and R$^3$ is acyl or —SO$_2$R$^6$, or R$^2$ and R$^3$ together with the nitrogen atom to which they are attached denote a 5- or 6-membered heterocyclic group, R$^4$ and R$^5$ are each independently hydrogen or $C_1$–$C_8$-alkyl, or R$^4$ and R$^5$ together with the nitrogen atom to which they are attached denote a 5- or 6-membered heterocyclic group, R$^6$ is $C_1$–$C_8$-alkyl, $C_1$–$C_8$-haloalkyl, or phenyl optionally substituted by $C_1$–$C_8$-alkyl, and n is 1, 2, 3 or 4, with the proviso that when Ar$^1$ is p-chlorophenyl and R$^1$ is hydrogen, Ar$^2$ is not phenyl or p-nitrophenyl.

Terms used in the specification have the following meanings:

"$C_1$–$C_8$-alkyl" as used herein denotes straight chain or branched $C_1$–$C_8$-alkyl, which may be, for example, methyl, ethyl, n-propyl, isopropyl, n-butyl, isobutyl, sec-butyl, tert-butyl, straight or branched pentyl, straight or branched hexyl, straight or branched heptyl, or straight or branched octyl. Preferably, $C_1$–$C_8$-alkyl is $C_1$–$C_4$-alkyl.

"$C_1$–$C_8$-alkoxy" as used herein denotes straight chain or branched $C_1$–$C_8$-alkoxy which may be, for example, methoxy, ethoxy, n-propoxy, isopropoxy, n-butoxy, isobutoxy, sec-butoxy, tert-butoxy, straight or branched pentoxy, straight or branched hexyloxy, straight or branched heptyloxy, or straight or branched octyloxy. Preferably, $C_1$–$C_8$-alkoxy is $C_1$–$C_4$-alkoxy.

"$C_1$–$C_8$-haloalkyl" as used herein denotes $C_1$–$C_8$-alkyl as hereinbefore defined substituted by one or more halogen atoms, preferably one, two or three halogen atoms.

"Acyl" as used herein denotes alkylcarbonyl, for example $C_1$–$C_8$-alkylcarbonyl where $C_1$–$C_8$-alkyl may be one of the $C_1$–$C_8$-alkyl groups hereinbefore mentioned, optionally substituted by one or more halogen atoms; cycloalkylcarbonyl, for example $C_3$–$C_8$-cycloalkylcarbonyl where $C_3$–$C_8$-cycloalkyl may be, for example, cyclopropyl, cyclobutyl, cyclopentyl, cyclohexyl, cycloheptyl or cyclooctyl; 5- or 6-membered heterocyclylcarbonyl having one or two hetero atoms selected from nitrogen, oxygen and sulfur in the ring, such as furylcarbonyl or pyridylcarbonyl; arylcarbonyl, for example $C_6$–$C_{10}$-arylcarbonyl such as benzoyl; or aralkylcarbonyl, for example $C_6$ to $C_{10}$-aryl-$C_1$–$C_4$-alkylcarbonyl such as benzylcarbonyl or phenylethylcarbonyl. Preferably acyl is $C_1$–$C_4$-alkylcarbonyl.

"Acyloxy" as used herein denotes alkylcarbonyloxy, for example $C_1$–$C_8$-alkylcarbonyloxy where $C_1$–$C_8$-alkyl may be one of the $C_1$–$C_8$-alkyl groups hereinbefore mentioned, optionally substituted by one or more halogen atoms; cycloalkylcarbonyloxy, for example $C_3$–$C_8$-cycloalkylcarbonyloxy where $C_3$–C8-cycloalkyl may be, for example, cyclopropyl, cyclobutyl, cyclopentyl, cyclohexyl, cycloheptyl or cyclooctyl; 5- or 6-membered heterocyclylcarbonyloxy having one or two hetero atoms selected from nitrogen, oxygen and sulfur in the ring, such as furylcarbonyloxy or pyridylcarbonyloxy; arylcarbonyloxy, for example $C_6$–$C_{10}$-arylcarbonyloxy such as benzoyloxy; or aralkylcarbonyloxy, for example $C_6$ to $C_{10}$-aryl-$C_1$–$C_4$-alkylcarbonyloxy such as benzylcarbonyloxy or phenylethylcarbonyloxy. Preferably acyloxy is $C_1$–$C_4$-alkylcarbonyloxy.

"Halogen" as used herein may be fluorine, chlorine, bromine or iodine; preferably it is fluorine, chlorine or bromine.

In Ar$^1$, the phenyl group may be substituted by one, two or three, preferably one or two halogen atoms, preferably selected from fluorine and chlorine atoms. When there is one halogen substituent, it is preferably para to the indicated carbonyl group. When there are two or three halogen substituents, preferably one is para to the indicated carbonyl group and at least one of the others is ortho to the indicated carbonyl group.

Ar$^2$ as substituted phenyl may, for example, be substituted by one, two, three, four or five, preferably by one, two or three, of the abovementioned substituents. Ar$^2$ may be, for example, monosubstituted phenyl in which the substituent, preferably halogen, cyano, nitro or $C_1$–$C_4$-alkoxy, is preferably ortho or meta to the indicated —CH=CH— group. Ar$^2$ may alternatively be, for example, disubstituted phenyl in which the substituents are preferably selected from halogen, cyano, hydroxy, nitro, $C_1$–$C_4$-alkoxy, $C_1$–$C_4$-alkyl and $C_1$–$C_4$-haloalkyl, especially two halogen substituents (same or different halogen), two $C_1$–$C_4$-alkoxy groups, two $C_1$–$C_4$-alkyl groups, two $C_1$–$C_4$-haloalkyl groups, one halogen and one cyano, one halogen and one $C_1$–$C_4$-alkoxy, one halogen and one nitro, one halogen and one hydroxy, one halogen and one $C_1$–$C_4$-haloalkyl, one cyano and one $C_1$–$C_4$-alkoxy, one hydroxy and one $C_1$–$C_4$-alkyl, or one hydroxy and one $C_1$–$C_4$-alkoxy group. Ar$^2$ may alternatively be, for example, trisubstituted phenyl in which the substituents are preferably selected from halogen, hydroxy, $C_1$–$C_4$-alkoxy and $C_1$–$C_4$-alkoxycarbonyl, especially three halogen substituents (same or two or three different halogens), or two $C_1$–$C_4$-alkoxy and one halogen, hydroxy or $C_1$–$C_4$-alkoxycarbonyl. Ar$^2$ may alternatively be, for example, penta-substituted phenyl in which the substituents are preferably halogen, especially fluorine. Especially preferred groups Ar$^2$ are cyanophenyl, particularly meta-cyanophenyl, and disubstituted phenyl where one substituent is $C_1$–$C_4$-alkoxy, preferably ortho to the —CH=CH— group, and the other, preferably para to the $C_1$–$C_4$-alkoxy group, is $C_1$–$C_4$-alkoxy, halogen, cyano or $C_1$–$C_4$-alkyl.

R$^1$ as optionally substituted $C_1$–$C_8$-alkyl is preferably optionally substituted $C_1$–$C_4$-alkyl, especially $C_1$–$C_4$-alkyl or substituted methyl or ethyl. When R$^1$ is substituted by a cyclic organic group, the latter may be a carbocyclic or heterocyclic group, for example a $C_3$–$C_{15}$-carbocyclic group or a 5- to 7-membered heterocyclic group having one or more, preferably one, two or three, ring hetero atoms selected from nitrogen, oxygen and sulfur. The $C_3$–$C_{15}$-carbocyclic group may be, for example, a cycloaliphatic group having 3 to 8 carbon atoms, preferably $C_5$- or $C_6$-cycloalkyl such as cyclopentyl, methylcyclopentyl or cyclohexyl. The $C_3$–$C_{15}$-carbocyclic group may alternatively be, for example, a $C_6$–$C_{15}$ aromatic group, such as phenyl, which is unsubstituted or substituted by $C_1$–$C_8$-alkyl, $C_1$–$C_8$-alkoxy, halogen, cyano, —$CON(R^4)R^5$, —$SO_2N(R^4)R^5$ or $C_1$–$C_8$-alkylsulfonylamino where $R^4$ and $R^5$ are a hereinbefore defined. The heterocyclic group may have one nitrogen, oxygen or sulfur atom in the ring or it may have two nitrogens, or one oxygen and one or two nitrogens, or one sulfur and one or two nitrogens in the ring. The heterocyclic group is preferably a heterocyclic aromatic group, especially a 5- or 6-membered heterocyclic group such as furyl, imidazolyl, thiazolyl or pyridyl. In especially preferred compounds, $R^1$ is $C_1$–$C_4$-alkyl substituted by hydroxy, phenyl, or a 5-or 6-membered heterocyclic aromatic group having one or two ring hetero atoms selected from nitrogen, oxygen and sulfur.

Preferred compounds of formula I in free or salt form include those in which $Ar^1$ is phenyl substituted by fluorine or chlorine para to the indicated carbonyl group and optionally further substituted by halogen ortho to the indicated carbonyl group, $Ar^2$ is phenyl monosubstituted by a substituent selected from halogen, cyano, nitro and $C_1$–$C_4$-alkoxy, phenyl substituted by two substituents, which may be the same or different, selected from halogen, cyano, hydroxy, $C_1$–$C_4$-alkoxy, $C_1$–$C_4$-alkyl, $C_1$–$C_4$-haloalkyl and nitro, or phenyl substituted by three substituents, which may be the same or different, selected from halogen, hydroxy, $C_1$–$C_4$-alkoxy and $C_1$–$C_4$-alkoxycarbonyl, $R^1$ is hydrogen, $C_1$–$C_4$-alkyl or $C_1$–$C_4$-alkyl substituted by hydroxy, $C_3$–$C_8$-cycloalkyl, phenyl, $C_1$–$C_4$-alkylsulfonylamino-substituted phenyl or a 5- or 6-membered heterocyclic aromatic group having one or more ring hetero atoms selected from nitrogen, oxygen and sulfur, and n is 1 or 2.

Further preferred compounds of formula I in free or salt form include those in which $Ar^1$ is phenyl substituted by fluorine or chlorine para to the indicated carbonyl group, $Ar^2$ is phenyl substituted ortho to the indicated —CH=CH— group by $C_1$–$C_4$-alkoxy and para to the $C_1$–$C_4$-alkoxy group by cyano, halogen or $C_1$–$C_4$-alkoxy, $R^1$ is $C_1$–$C_4$-alkyl substituted by hydroxy, phenyl, $C_1$–$C_4$-alkylsulfonylamino-substituted phenyl or a 5- or 6-membered heterocyclic aromatic group having one or two ring hetero atoms selected from nitrogen, oxygen and sulfur, and n is 1.

The compounds represented by formula I are capable of forming acid addition salts, particularly pharmaceutically acceptable acid addition salts. Pharmaceutically acceptable acid addition salts of the compound of formula I include those of inorganic acids, for example, hydrohalic acids such as hydrofluoric acid, hydrochloric acid, hydrobromic acid or hydroiodic acid, nitric acid, sulfuric acid, phosphoric acid; and organic acids, for example aliphatic monocarboxylic acids such as formic acid, acetic acid, trifluoroacetic acid, propionic acid and butyric acid, aliphatic hydroxy acids such as lactic acid, citric acid, tartaric acid or malic acid, dicarboxylic acids such as maleic acid or succinic acid, aromatic carboxylic acids such as benzoic acid, p-chlorobenzoic acid, diphenylacetic acid or triphenylacetic acid, aromatic hydroxy acids such as o-hydroxybenzoic acid, p-hydroxybenzoic acid, 1-hydroxynaphthalene-2-carboxylic acid or 3-hydroxynaphthalene-2-carboxylic acid, and sulfonic acids such as methanesulfonic acid or benzenesulfonic acid. These salts may be prepared from compounds of formula I by known salt-forming procedures.

Compounds of formula I which contain acidic, e.g. carboxyl, groups, are also capable of forming salts with bases, in particular pharmaceutically acceptable bases such as those well known in the art; suitable such salts include metal salts, particularly alkali metal or alkaline earth metal salts such as sodium, potassium, magnesium or calcium salts, or salts with ammonia or pharmaceutically acceptable organic amines or heterocyclic bases such as ethanolamines, benzylamines or pyridine. These salts may be prepared from compounds of formula I by known salt-forming procedures.

When $R^1$ is other than hydrogen, the carbon atom to which $R^1$ is attached in formula I is asymmetric, in which case the compounds exist in individual optically active isomeric forms or as mixtures thereof, e.g. as racemic or diastereomeric mixtures. The invention embraces both individual optically active R and S isomers as well as mixtures, e.g. racemic or diastereomeric mixtures, thereof.

Specific especially preferred compounds of the invention are those described hereinafter in the Examples, particularly those of Examples 4, 9, 10, 15, 18, 19, 20, 21, 23, 24, 25, 28, 29, 30, 37, 38,40, 42, 43, 44 and 45.

The invention also provides a process for the preparation of compounds of formula I which comprises (i) (A) reacting a compound of formula

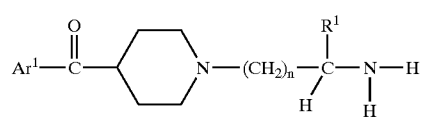

II with a compound of formula

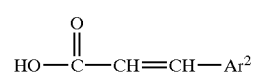

III or an amide-forming derivative thereof, where $Ar^1$, $Ar^2$, $R^1$ and n are as hereinbefore defined, or (B) reacting a compound of formula m, or an amide forming derivative thereof, with a compound of formula

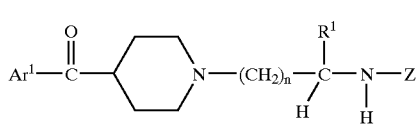

IV where $Ar^1$, $R^1$ and n are as hereinbefore defined and Z denotes a solid phase substrate chemically linked to the indicated nitrogen atom, and detaching the resulting product from the substrate to replace Z by hydrogen; and (ii) recovering the product in free or salt form.

In process variant (A), the compound of formula II may be in free or salt form. Process variant (A) may be effected using known methods, for example by reacting a compound of formula II with an acid halide, particularly acid chloride, of the acid of formula III using known amide-forming procedures. Conveniently, the compound of formula II in free or salt form is reacted with a free carboxylic acid of formula III, for example using known procedures, such as reaction in the presence of a tertiary amine and a peptide coupling agent such as a phosphonium salt, 2-(1H benzotriazol-1-yl)-1,1,3,3-tetramethyluronium tetrafluoroborate or diisopropylcarbodiimide; this reaction may be carried out in an inert organic solvent, for example a halohydrocarbon such as dichloromethane; the reaction temperature is conveniently from 0 to 40° C., preferably ambient temperature.

In another method of effecting process variant (A), a compound of formula II, preferably in salt form, is reacted with an amide-forming derivative of the acid of formula III which is a thioester of formula

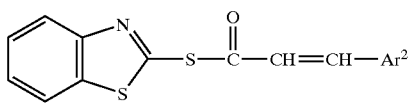

IIIA where $Ar^2$ is as hereinbefore defined. The reaction may be carried using known procedures or analogously as described hereinafter in the Examples. It may be effected in the presence of a tertiary base such as N-methylmorpholine. It is conveniently effected in an organic solvent, preferably an alcohol such as ethanol. The reaction temperature may be, for example, from 30 to 60° C., conveniently from 40 to 50° C.

Process variant (B) may be effected using known methods, for example by reacting the substrate-bound compound with the free acid under known peptide coupling conditions, for example in the presence of a tertiary amine and a peptide coupling agent such as those mentioned above. The reaction may be effected in an inert organic solvent such as dimethylformamide (DMF). Suitable reaction temperatures are from 0 to 40° C., e.g. 15 to 25° C. The product may be detached from the substrate in a known manner, for example, where the N atom is linked to a $CH_2$ of a benzyl group in Z, by treatment with trifluoroacetic acid.

Compounds of formula III are either available commercially or may be prepared by known methods. Compounds of formula IIIA may be obtained by reaction of an acid of formula III with 2,2'-dibenzothiazolyl disulfide in the presence of triphenylphosphine and a tertiary base such as N-methylmorpholine, e.g. as described in the Examples.

Compounds of formula II may be prepared by reacting a compound of formula

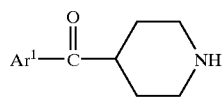

V with a compound of formula

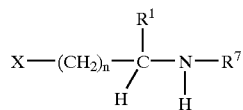

VI where $Ar^1$, $R^1$ and n are as hereinbefore defined, with the proviso that when $R^1$ contains a reactive functional group such as a hydroxy group, the reactive group may be in protected form, for example a hydroxy group protected as a tert-butoxy group, $R^7$ is hydrogen or an amine-protective group, for example a tert-butoxycarbonyl group, and X is halogen and, where $R^7$ is a protective group, replacing $R^7$ in the product by hydrogen, and, where $R^1$ in the product contains a protected functional group, replacing the protecting group by hydrogen. When $R^7$ is hydrogen, reaction between a compound of formula V and a salt of a compound of formula VI may be effected by the procedures described in U.S. Pat. No. 4,559,349. When $R^7$ is a protective group, reaction between compounds of formulae V and VI may be effected using known methods, for example in the presence of a tertiary organic base such as triethylamine or 1,8-diazabicyclo[5.4.0]undec-7-ene (DBU), conveniently in an inert organic solvent, for example a polar solvent such as dimethylformamide, the reaction temperature suitably being from 0 to 40° C., preferably ambient temperature. Replacement of a protective group $R^7$ by hydrogen may be effected using known procedures; for example, where $R^7$ is tert-butoxycarbonyl, by treatment with a carboxylic acid such as trifluoroacetic acid. Replacement of a protecting group in $R^1$ may be affected using known procedures, for example, when $R^1$ contains a hydroxy group protected as an ether group, such as tert-butoxy, by treatment with HBr in a carboxylic acid such as acetic acid; when $R^7$ is a protective group, this treatment also replaces $R^7$ by hydrogen. Compounds of formulae V and VI are known or may be prepared by known procedures.

Where reference is made herein to protected functional groups or to protecting groups, the protecting groups may be chosen in accordance with the nature of the functional group, for example as described in Protective Groups in Organic Synthesis, T. W. Greene and P. G. M. Wuts, John Wiley & Sons Inc, Second Edition, 1991, which reference also describes procedures suitable for replacement of the protecting groups by hydrogen.

Compounds of formula II may also be prepared by reacting a compound of formula V with a compound of formula

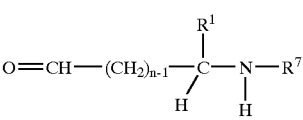

VII where $R^1$, $R^7$ and n are as hereinbefore defined and a reducing agent such as sodium cyanoborohydride or sodium triacetoxyborohydride, for example using known reductive amination procedures, conveniently in an inert organic solvent, for example an ether such as tetrahydrofuran (THF), the reaction temperature suitably being from 0 to 40° C., and, where $R^7$ is a protective group, replacing it by hydrogen. Compounds of formula VII are known or may be prepared by known procedures.

Compounds of formula II where $R^1$ is hydroxymethyl may also be prepared by reacting a compound of formula V with (R)4-formyl-2,2-dimethyl-oxazolidine-3-carboxylic acid tert-butyl ester, of formula

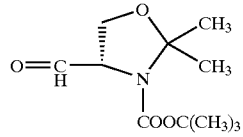

VIIa and a reducing agent such as sodium triacetoxyborohydride, for example under conditions described above for reaction of compounds of formulae V and VII, and reacting the product with a suitable reagent to cleave the oxazolidine ring and replace the nitrogen-bound ester group by hydrogen, for example hydrogen chloride in ethanol or dioxane as described hereinafter in the Examples, in which case the compound of formula II is obtained as a hydrochloride salt. The reaction product of the compounds of formulae V and VIIa may, e.g. where it is desired to improve enantiometric purity, be treated with an optically active acid such as di-O,O-benzoyl-L-tartaric acid before cleavage of the oxazolidine ring. The compound of formula VIIa may be prepared as described by A D Campbell et al, Synthesis 1707–1709 (1998) or G Ageno et al, Tetrahedron 51, 8121–8134 (1995).

Compounds of formula II where $R^1$ is $C_1$–$C_8$-alkoxymethyl or acyloxymethyl can be prepared by appropriate etherification or acylation of compounds of formula II where $R^1$ is hydroxymethyl.

Compounds of formula IV may be prepared by reacting a compound of formula V with a compound of formula

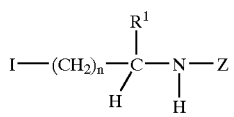

VIII where $R^1$, Z and n are as hereinbefore defined, for example using known procedures such as reaction in an inert organic solvent such as DMF in the presence of a tertiary amine, conveniently at a temperature of 40 to 60° C. Compounds of formula VIII may be prepared by reaction of a compound of formula

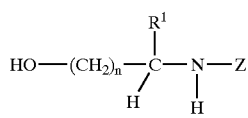

IX where $R^1$, Z and n are as hereinbefore defined, with iodine, for example using known procedures such as reaction in an inert organic solvent such as a mixture of THF and acetonitrile in the presence of a triarylphosphine and imidazole, conveniently at a temperature of 10 to 40° C. Compounds of formula IX may be prepared by reaction of a compound of formula

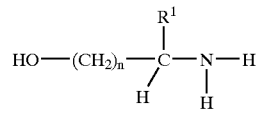

X where where $R^1$ and n are as hereinbefore defined, with a solid phase substrate Z having a group, such as an aldehyde group, reactive with amino. Such solid phase substrates, including modified resins, particularly modified polystyrene resins, are commercially available. Compounds of formula X are known or may be prepared by known methods.

Compounds of formula I in free form may be converted into salt form, and vice versa, in a conventional manner. The compounds in free or salt form can be obtained in the form of hydrates or solvates containing a solvent used for crystallization. Compounds of formula I can be recovered from reaction mixtures and purified in a conventional manner. Isomers, such as enantiomers, may be obtained in a conventional manner, e.g. by fractional crystallization or asymmetric synthesis from correspondingly asymmetrically substituted, e.g. optically active, starting materials.

Compounds of formula I in free or pharmaceutically acceptable salt form, hereinafter referred to alternatively as agents of the invention, are useful as pharmaceuticals. Accordingly the invention also provides a compound of formula I in free or pharmaceutically acceptable salt form for use as a pharmaceutical. The agents of the invention act as CCR-3 receptor antagonists, thereby inhibiting the infiltration and activation of inflammatory cells, particularly eosinophils, and inhibiting allergic response. The inhibitory properties of agents of the invention can be demonstrated in the following assay:

CCR-3 Binding Assay

In this assay the effect of agents of the invention on the binding of human eotaxin to human CCR-3 is determined. Recombinant cells expressing human CCR-3 are captured by wheatgerm agglutinin (WGA) polyvinyltoluidene (PVT) SPA beads (available from Amersham), through a specific interaction between the WGA and carbohydrate residues of glycoproteins on the surface of the cells. [$^{125}$I]-human eotaxin (available from Amersham) binds specifically to CCR-3 receptors bringing the [$^{125}$I]-human eotaxin in close proximity to the SPA beads. Emitted â-particles from the [$^{125}$I]-human eotaxin excite, by its proximity, the fluorophore in the beads and produce light. Free [$^{125}$I]-human eotaxin in solution is not in close proximity to the scintillant and hence does not produce light. The scintillation count is therefore a measure of the extent to which the test compound inhibits binding of the eotaxin to the CCR-3.

Preparation of Assay Buffer: 5.96 g HEPES and 7.0 g sodium chloride are dissolved in distilled water and 1M aqueous $CaCl_2$ (1 mL) and 1M aqueous $MgCl_2$ (5 mL) are added. The pH is adjusted to 7.6 with NaOH and the solution made to a final volume of 1 L using distilled water. 5 g bovine serum albumin and 0.1 g sodium azide are then dissolved in the solution and the resulting buffer stored at 4° C. A Complete™ protease inhibitor cocktail tablet (available from Boehringer) is added per 50 mL of the buffer on the day of use.

Preparation of Homogenisation Buffer: Tris-base (2.42 g) is dissolved in distilled water, the pH of the solution is adjusted to 7.6 with hydrochloric acid and the solution is diluted with distilled water to a final volume of 1L. The resulting buffer is stored at 4° C. A Complete™ protease inhibitor cocktail tablet is added per 50 mL of the buffer on the day of use.

Preparation of membranes: Confluent rat basophil leukemia (RBL-2H3) cells stably expressing CCR3 are removed from tissue culture flasks using enzyme-free cell dissociation buffer and resuspended in phosphate-buffered saline. The cells are centrifuged (800 g, 5 minutes), the pellet resuspended in ice-cold homogenisation buffer using 1 mL homogenisation buffer per gram of cells and incubated on ice for 30 minutes. The cells are homogenised on ice with 10 strokes in a glass mortar and pestle. The homogenate is centrifuged (800 g, 5 minutes, 4° C.), the supernatant further centrifuged (48,000 g, 30 minutes, 4° C.) and the pellet redissolved in Homogenisation Buffer containing 10% (v/v) glycerol. The protein content of the membrane preparation is estimated by the method of Bradford (Anal.Biochem. (1976) 72:248) and aliquots are snap frozen and stored at −80° C. The assay is performed in a final volume of 250 μL per well of an Optiplate (ex Canberra Packard). To selected wells of the Optiplate are added 50 μL of solutions of a test compound in Assay Buffer containing 5% DMSO (concentrations from 0.1 nM to 10 μM). To determine total binding, 50 μL of the Assay Buffer containing 5% DMSO is added to other selected wells. To determine non-specific binding, 50 μL of 100 nM human eotaxin (ex R&D Systems) in Assay Buffer containing 5% DMSO is added to further selected wells. To all wells are added 50 μL [$^{125}$I]-Human eotaxin (ex Amersham) in Assay Buffer containing 5% DMSO at a concentration of 250 pM (to give a final concentration of 50 pM per well), 50 μL of WGA-PVT SPA beads in Assay Buffer (to give a final concentration of 1.0 mg beads per well) and 100 μL of the membrane preparation at a concentration of 100 μg protein in Assay Buffer (to give a final concentration of 10 μg protein per well). The plate is then incubated for 4 hours at room temperature. The plate is sealed using TopSeal-S (ex Canberra Packard) according to the manufacturer's instructions. The resulting scintillations are counted using a Canberra Packard TopCount, each well being counted for 1 minute. The concentration of test compound at which 50% inhibition occurs ($IC_{50}$) is determined from concentration-inhibition curves in a conventional manner.

The compounds of the Examples hereinbelow have $IC_{50}$ values below 1 μM in the above assay. For instance, the compounds of Examples 1, 2, 4, 7, 9, 13, 20, 23, 25, 28, 30, 38, 40, 43 and 44 have $IC_{50}$(nM) values of 125, 68, 13, 15, 5, 26, 8, 10, 11, 2, 13, 14, 6, 22 and 25 respectively.

Most of the compounds of the Examples exhibit selectivity for inhibition of CCR-3 binding relative to inhibition of binding of the alpha-1 adrenergic receptor. The inhibitory properties of agents of the invention on binding of the alpha-1 adrenergic receptor can be determined in the following assay:

Cerebral cortices from male Sprague-Dawley rats (175–200 g) are dissected and homogenised in 10 volumes of ice cold 0.32 M sucrose (containing 1 mM $MgCl_2$ dihydrate and 1 mM $K_2HPO_4$) with a glass/teflon homogeniser. The membranes are centrifuged at 1000×g for 15 min., the pellet discarded and the centrifugation repeated. The supernatants are pooled and centrifuged at 18,000×g for 15 min. The pellet is osmotically shocked in 10 volumes of water and kept on ice for 30 min. The suspension is centrifuged at 39,000×g for 20 min., resuspended in Krebs-Henseleit buffer pH 7.4 (1.17 mM $MgSO_4$ anhydrous, 4.69 mM KCl, 0.7 mM $K_2HPO_4$ anhydrous, 0.11M NaCl, 11 mM D-glucose and 25 mM $NaHCO_3$) containing 20 mM Tris, and kept for 2 days at −20° C. The membranes are then thawed at 20–23° C., washed three times with Krebs-Henseleit buffer by centrifugation at 18,000×g for 15 min., left overnight at 4° C. and washed again three times. The final pellet is resuspended with a glass/teflon homogeniser in 125 mL/100 membranes in the same buffer. A sample is taken to determine the protein concentration (using the Bradford Assay with gamma globulin as the standard) and the remainder aliquoted and stored at −80° C.

The resulting membranes are subjected to a radioligand binding assay. The assay is conducted in triplicate using 96 well plates containing [$^{125}$I]-HEAT (Amersham) (40 pM, $K_d$: 58.9±18.7 pM), unlabelled test compound and membrane (57.1 μg/mL) to yield a final volume of 250 μl (assay buffer containing 50 mM Tris-base and 0.9% (w/v) NaCl, pH 7.4). The plates are incubated at 37° C. for 60 min., after which rapid vacuum filtration over Whatman GF/C 96 well filter plates is carried out. Each plate is then washed three times with 10 ml of ice cold assay buffer using a Brandel Cell harvester (Gaithersburg, Md.). Following drying of the plates for 3 h. at 50° C., 40 μL of Microscint 20 is added to each well, the plates incubated at room temperature for a further 20 min. and the retained radioactivity quantified in a Packard Topcount NXT scintillation counter.

Stock solutions of test compounds are dissolved initially in 100% DMSO and diluted with assay buffer to the required concentrations to yield 1% (v/v) DMSO.

The concentration of test compound at which 50% inhibition occurs ($IC_{50}$) is determined from concentration-inhibition curves in a conventional manner. Compounds of Examples 1, 2, 4, 7, 9, 13, 20, 23, 25, 28, 30, 38, 40, 43 and 44 have $IC_{50}$(nM) values of 210, 221, 94, 48, 58, 53, 89, 131, 387, 72, 121, 1519, 215, 356 and 331 in this assay.

Having regard to their inhibition of binding of CCR-3, agents of the invention are useful in the treatment of conditions mediated by CCR-3, particularly inflammatory or allergic conditions. Treatment in accordance with the invention may be symptomatic or prophylactic.

Accordingly, agents of the invention are useful in the treatment of inflammatory or obstructive airways diseases, resulting, for example, in reduction of tissue damage, bronchial hyperreactivity, remodelling or disease progression. Inflammatory or obstructive airways diseases to which the present invention is applicable include asthma of whatever type or genesis including both intrinsic (non-allergic) asthma and extrinsic (allergic) asthma, mild asthma, moderate asthma, severe asthma, bronchitic asthma, excercise-induced asthma, occupational asthma and asthma induced following bacterial or viral infection. Treatment of asthma is also to be understood as embracing treatment of subjects, e.g. of less than 4 or 5 years of age, exhibiting wheezing symptoms and diagnosed or diagnosable as "wheezy infants", an established patient category of major medical concern and now often identified as incipient or early-phase asthmatics. (For convenience this particular asthmatic condition is referred to as "wheezy-infant syndrome".)

Prophylactic efficacy in the treatment of asthma will be evidenced by reduced frequency or severity of symptomatic attack, e.g. of acute asthmatic or bronchoconstrictor attack, improvement in lung function or improved airways hyper-reactivity. It may further be evidenced by reduced requirement for other, symptomatic therapy, i.e. therapy for or intended to restrict or abort symptomatic attack when it occurs, for example anti-inflammatory (e.g. corticosteroid) or bronchodilatory. Prophylactic benefit in asthma may in particular be apparent in subjects prone to "morning dipping". "Morning dipping" is a recognised asthmatic syndrome, common to a substantial percentage of asthimatics and characterised by asthma attack, e.g. between the hours of about 4 to 6 am, i.e. at a time normally substantially distant form any previously administered symptomatic asthma therapy.

Other inflammatory or obstructive airways diseases and conditions to which the present invention is applicable include acute lung injury (ALI), acute/adult respiratory distress syndrome (ARDS), chronic obstructive pulmonary, airways or lung disease (COPD, COAD or COLD), including chronic bronchitis or dyspnea associated therewith, emphysema, as well as exacerbation of airways hyperreactivity consequent to other drug therapy, in particular other inhaled drug therapy. The invention is also applicable to the treatment of bronchitis of whatever type or genesis including, e.g., acute, arachidic, catarrhal, croupus, chronic or phthinoid bronchitis. Further inflammatory or obstructive airways diseases to which the present invention is applicable include pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siderosis, silicosis, tabacosis and byssinosis.

Having regard to their anti-inflammatory activity, in particular in relation to inhibition of eosinophil activation, agents of the invention are also useful in the treatment of eosinophil related disorders, e.g. eosinophilia, in particular eosinophil related disorders of the airways (e.g. involving morbid eosinophilic infiltration of pulmonary tissues) including hypereosinophilia as it effects the airways and/or lungs as well as, for example, eosinophil-related disorders of the airways consequential or concomitant to Löffler's syndrome, eosinophilic pneumonia, parasitic (in particular metazoan) infestation (including tropical eosinophilia), bronchopulmonary aspergillosis, polyarteritis nodosa (including Churg-Strauss syndrome), eosinophilic granuloma and eosinophil-related disorders affecting the airways occasioned by drug-reaction.

Agents of the invention are also useful in the treatment of inflammatory or allergic conditions of the skin, for example psoriasis, contact dermatitis, atopic dermatitis, alopecia areata, erythema multiforma, dermatitis herpetiformis, scleroderma, vitiligo, hypersensitivity angiitis, urticaria, bullous pemphigoid, lupus erythematosus, pemphisus, epidermolysis bullosa acquisita, and other inflammatory or allergic conditions of the skin.

Agents of the invention may also be used for the treatment of other diseases or conditions, in particular diseases or conditions having an inflammatory component, for example, treatment of diseases and conditions of the eye such as conjunctivitis, keratoconjunctivitis sicca, and vernal conjunctivitis, diseases affecting the nose including allergic rhinitis, e.g. atrophic, chronic, or seasonal rhinitis, inflammatory conditions of the gastrointestinal tract, for example inflammatory bowel disease such as ulcerative colitis and Crohn's disease, diseases of the bone and joints including rheumatoid arthritis, psoriatic arthritis, ankylosing spondylitis and systemic sclerosis, and other diseases such as athersclerosis, multiple sclerosis, diabetes (type I), myasthenia gravis, hyper IgE syndrome and acute and chronic allograft rejection, e.g. following transplantation of heart, kidney, liver, lung or bone marrow.

The effectiveness of an agent of the invention in inhibiting inflammatory conditions, for example in inflammatory airways diseases, may be demonstrated in an animal model, e.g. a mouse or rat model, of airways inflammation or other inflammatory conditions, for example as described by Szarka et al, J. Immunol. Methods (1997) 202:49–57; Renzi et al, Am. Rev. Respir. Dis. (1993) 148:932–939; Tsuyuki et al., J. Clin. Invest. (1995) 96:2924–2931; and Cernadas et al (1999) Am. J. Respir. Cell Mol. Biol. 20:1–8.

The agents of the invention are also useful as co-therapeutic agents for use in combination with other drug substances such as anti-inflammatory, bronchodilatory or antihistamine drug substances, particularly in the treatment of obstructive or inflammatory airways diseases such as those mentioned hereinbefore, for example as potentiators of therapeutic activity of such drugs or as a means of reducing required dosaging or potential side effects of such drugs. An agent of the invention may be mixed with the other drug substance in a fixed pharmaceutical composition or it may be administered separately, before, simultaneously with or after the other drug substance. Such anti-inflammatory drugs include steroids, in particular glucocorticosteroids such as budesonide, beclamethasone, fluticasone, ciclesonide or mometasone, LTB4 antagonists such as those described in U.S. Pat. No. 5,451,700, LTD4 antagonists such as montelukast and zafirlukast, dopamine receptor agonists such as cabergoline, bromocriptine, ropinirole and 4-hydroxy-7-[2-[[2-[[3-(2-phenylethoxy)propyl]sulfonyl]ethyl]-amino]ethyl]-2(3H)-benzothiazolone and pharmaceutically acceptable salts thereof (the hydrochloride being Viozan®— AstraZeneca), and PDE4 inhibitors such as Ariflo® (GlaxoSmith Kline), Roflumilast (Byk Gulden), V-11294A (Napp), BAY19-8004 (Bayer), SCH-351591 (Schering-Plough), and PD189659 (Parke-Davis). Such bronchodilatory drugs include anticholinergic or antimuscarinic agents, in particular ipratropium bromide, oxitropium bromide and tiotropium bromide, and beta-2 adrenoceptor agonists such as salbutamol, terbutaline, salmeterol and, especially, formoterol and pharmaceutically acceptable salts thereof, and compounds (in free or salt or solvate form) of formula I of PCT International Publication No. WO00/75114, which document is incorporated herein by reference, preferably compounds of the Examples thereof, especially a compound of formula

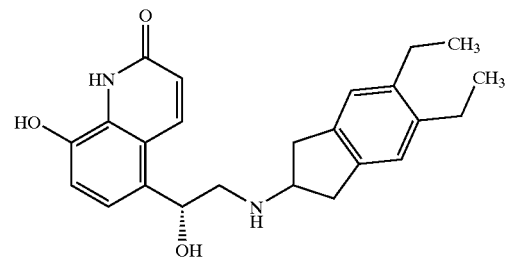

and pharmaceutically acceptable salts thereof. Co-therapeutic antihistamine drug substances include cetirizine hydrochloride, acetaminophen, clemastine fumarate, promethazine, loratidine, desloratidine, diphenhydramine and fexofenadine hydrochloride. Combinations of agents of the invention and steroids, beta-2 agonists, PDE4 inhibitors or LTD4 antagonists may be used, for example, in the treatment of COPD or, particularly, asthma. Combinations of agents of the invention and anticholinergic or antimuscarinic agents, PDE4 inhibitors, dopamine receptor agonists or LTB4 antagonists may be used, for example, in the treatment of asthma or, particularly, COPD.

Other useful combinations of agents of the invention with anti-inflammatory drugs are those with other anatagonists of chemokine receptors, e.g. CCR-1, CCR-2, CCR-3, CCR-4, CCR-5, CCR-6, CCR-7, CCR-8, CCR-9 and CCR10, CXCR1, CXCR2, CXCR3, CXCR4, CXCR5, particularly CCR-5 antagonists such as Schering-Plough antagonists SC-351125, SCH-55700 and SCH-D, Takeda antagonists such as N-[[4-[[[6,7-dihydro-2-(4-methylphenyl)-5H-benzocyclohepten-8-yl]carbonyl]amino]phenyl]-methyl] tetrahydro-N,N-dimethyl-2H-pyran-4-aminium chloride (TAK-770), and CCR-5 antagonists described in U.S. Pat. No. 6,166,037 (particularly claims 18 and 19), WO00/66558 (particularly claim 8), and WO00/66559 (particularly claim 9).

In accordance with the foregoing, the invention also provides a method for the treatment of a condition mediated by CCR-3, for example an inflammatory or allergic condition, particularly an inflammatory or obstructive airways disease, which comprises administering to a subject, particularly a human subject, in need thereof an effective amount of a compound of formula I in a free or pharmaceutically acceptable salt form as hereinbefore described. In another aspect the invention provides the use of a compound of formula I, in free or pharmaceutically acceptable salt form, as hereinbefore described for the manufacture of a medicament for the treatment of a condition mediated by CCR-3, for example an inflammatory or allergic condition, particularly an inflammatory or obstructive airways disease.

The agents of the invention may be administered by any appropriate route, e.g. orally, for example in the form of a tablet or capsule; parenterally, for example intravenously; by inhalation, for example in the treatment of inflammatory or obstructive airways disease; intranasally, for example in the treatment of allergic rhinitis; topically to the skin, for example in the treatment of atopic dermatitis; or rectally, for example in the treatment of inflammatory bowel disease.

In a further aspect, the invention also provides a pharmaceutical composition comprising as active ingredient a compound of formula I in free or pharmaceutically acceptable salt form, optionally together with a pharmaceutically acceptable diluent or carrier therefor. The composition may contain a co-therapeutic agent such as an anti-inflammatory or bronchodilatory drug as hereinbefore described. Such compositions may be prepared using conventional diluents or excipients and techniques known in the galenic art. Thus oral dosage forms may include tablets and capsules. Formulations for topical administration may take the form of creams, ointments, gels or transdermal delivery systems, e.g. patches. Compositions for inhalation may comprise aerosol or other atomizable formulations or dry powder formulations.

The invention includes (A) an agent of the invention in inhalable form, e.g. in an aerosol or other atomisable composition or in inhalable particulate, e.g. micronised form, (B) an inhalable medicament comprising an agent of the invention in inhalable form; (C) a pharmaceutical product comprising such an agent of the invention in inhalable form in association with an inhalation device; and (D) an inhalation device containing an agent of the invention in inhalable form.

Dosages of agents of the invention employed in practising the present invention will of course vary depending, for example, on the particular condition to be treated, the effect desired and the mode of administration. In general, suitable daily dosages for administration by inhalation are of the order of 0.01 to 30 mg/kg while for oral administration suitable daily doses are of the order of 0.01 to 100 mg/kg.

The invention is illustrated by the following Examples.

EXAMPLES 1–47

Compounds of formula I which are also of formula

XI

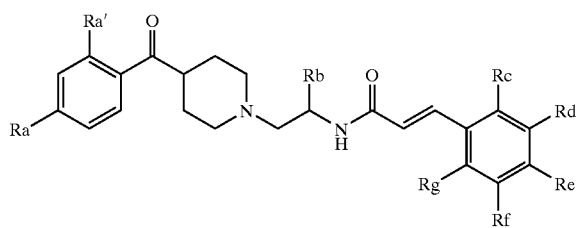

and their methods of preparation are shown in the following table, the methods being described hereinafter. Ra' is H in all Examples except Example 12, where it is F. The table also shows characterising mass spectrometry ([MH]$^+$) data and, where the Example is a salt, the identity of the salt-forming acid.

| Example No | Ra | Rb | Rc | Rd | Re | Rf | Rg | M/S | Salt form | Method |
|---|---|---|---|---|---|---|---|---|---|---|
| 1 | F | H | H | CN | H | H | H | 406.1 | CF$_3$CO$_2$H | C |
| 2 | F | 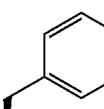 | H | CN | H | H | H | 496.8 | — | B |
| 3 | F | 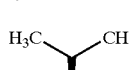 (H$_3$C, CH$_3$) | H | CN | H | H | H | 448.5 | — | B |
| 4 | F | 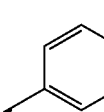 | OCH$_2$CH$_3$ | H | H | Br | H | 593.3 | — | B |
| 5 | F | H | H | CN | OCH$_3$ | H | H | 436.2 | CF$_3$CO$_2$H | C |

-continued

| Example No | Ra | Rb | Rc | Rd | Re | Rf | Rg | M/S | Salt form | Method |
|---|---|---|---|---|---|---|---|---|---|---|
| 6 | F | H | OCH₃ | H | H | OCH₃ | H | 441.3 | CF₃CO₂H | C |
| 7 | F | H | OCH₃ | H | H | Br | H | 491.2 | CF₃CO₂H | C |
| 8 | F | 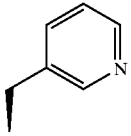 | H | CN | H | H | H | 497.4 | CH₃CO₂H | A |
| 9 | F | 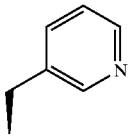 | OCH₃ | H | H | Br | H | 580.2 | — | A |
| 10 | F | H | OH | H | H | Cl | H | 431.7 | CF₃CO₂H | C |
| 11 | F | H | OCH₃ | H | H | F | H | 429.0 | CF₃CO₂H | C |
| 12 | F | H | OCH₃ | H | H | Br | H | 508.6 | CF₃CO₂H | C |
| 13 | Cl | H | OCH₃ | H | H | Br | H | 506.7 | CF₃CO₂H | C |
| 14 | F | H | OCH₃ | H | H | CN | H | 436.0 | CF₃CO₂H | C |
| 15 | F | H | OCH₃ | H | H | Cl | H | 445.2 | CF₃CO₂H | C |
| 16 | F | H | OCH₂CH₃ | H | H | Cl | H | 459.3 | CF₃CO₂H | C |
| 17 | F | H | O(CH₂)₂CH₃ | H | H | Cl | H | 473.3 | CF₃CO₂H | C |
| 18 | F | H | 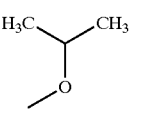 | H | H | Cl | H | 473.3 | CF₃CO₂H | C |
| 19 | F | H | O(CH₂)₂CH₃ | H | H | Br | H | 519.2 | CF₃CO₂H | C |
| 20 | F | H | 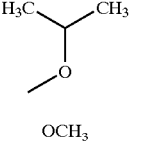 | H | H | Br | H | 519.2 | CF₃CO₂H | C |
| 21 | F | H | OCH₃ | H | H | CH₃ | H | 425.3 | CF₃CO₂H | C |
| 22 | F | H | 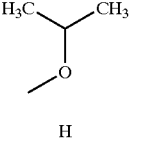 | H | H | CH₃ | H | 453.3 | CF₃CO₂H | C |
| 23 | F | 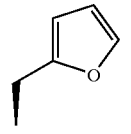 | H | H | H | CN | H | 486.4 | — | A |
| 24 | F | 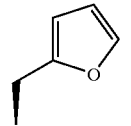 | OCH₃ | H | H | OCH₃ | H | 521.4 | — | A |
| 25 | F |  | OCH₃ | H | H | Br | H | 521.2 | — | B |
| 26 | F | 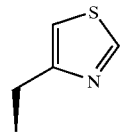 | H | H | H | CN | H | 503.4 | — | A |

-continued

| Example No | Ra | Rb | Rc | Rd | Re | Rf | Rg | M/S | Salt form | Method |
|---|---|---|---|---|---|---|---|---|---|---|
| 27 | F | 4-(CH₃SO₂NH)-benzyl | OCH₃ | H | H | OCH₃ | H | 624.4 | — | D, A |
| 28 | F | (furan-2-yl)methyl | OCH₃ | H | H | CN | H | 516.5 | — | A |
| 29 | F | (furan-2-yl)methyl | OCH₃ | H | H | Br | H | 571.1 | — | A |
| 30 | F | (1H-imidazol-4-yl)methyl | OCH₃ | H | H | CN | H | 516.6 | — | B |
| 31 | F | (furan-2-yl)methyl (stereo) | OCH₃ | H | H | CN | H | 516.5 | — | A |
| 32 | F | H | H | H | CH₃ | H | H | 395.4 | CF₃CO₂H | C |
| 33 | F | H | F | F | F | F | F | 471.3 | CF₃CO₂H | C |
| 34 | F | H | H | CF₃ | H | CF₃ | H | 517.4 | CF₃CO₂H | C |
| 35 | F | H | H | NO₂ | H | H | H | 426.3 | CF₃CO₂H | C |
| 36 | F | H | H | COOCH₃ | OCH₃ | H | OCH₃ | 499.9 | CF₃CO₂H | C |
| 37 | F | CH₂OH | OCH₃ | H | H | CN | H | 466.1 | — | F |
| 38 | Cl | CH₂OH | OCH₃ | H | H | CN | H | 482.2 | — | E |
| 39 | F | CH₃ | H | H | H | CN | H | 420.5 | — | B |
| 40 | Cl | CH₂OH | OCH₃ | H | H | Cl | H | 491.1 | CF₃CO₂H | C |
| 41 | Cl | H | OCH₃ | H | H | CN | H | 452.0 | CF₃CO₂H | C |
| 42 | F | CH₂CH₂OH | OCH₃ | H | H | Br | H | 533.3 | — | |

| Example No | Ra | Rb | Rc | Rd | Re | Rf | Rg | M/S | Salt form | Method |
|---|---|---|---|---|---|---|---|---|---|---|
| 43 | Cl |  | OCH₃ | H | H | Br | H | 537.0 | — | E |
| 44 | F | 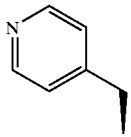 | OCH₃ | H | H | CN | H | 527.6 | — | A |
| 45 | F |  | OCH₃ | H | H | CN | H | 480.5 | — | F |
| 46 | Cl |  | OCH₃ | H | H | CN | H | 482 | 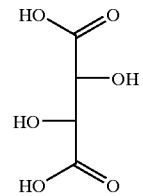 | G |
| 47 | Cl |  | OCH₃ | H | H | CN | H | 482 | — | G |

Method A
Preparation of ((R)-2-Hydroxy-1-pyridin-3-ylmethyl-ethyl)-carbamic Acid tert-Butyl Ester To a solution of (R)-2-.tert.-butoxycarbonylarino-3-pyridin-3-yl-propionic acid (0.9 g, 3.37 mmol) in dimethoxyethane (18 ml) is added N-methylmorpholine (0.44 ml, 4.04 mmol) and isobutylchloroformate (0.48 ml, 3.71 mmol). The reaction mixture is stirred at ambient temperature for 20 minutes and then filtered. The filtrate is treated with aqueous sodium borohydride solution (25 ml, 10.11 mmol) and the reaction mixture diluted immediately with water (200 ml). Stirring is continued for 1 hr at ambient temperature. The reaction mixture is partitioned between ethylacetate and water. The organic phase is separated, dried over magnesium sulphate and evaporated. The crude product is purified by flash silica chromatography (EtOAc elution) to afford ((R)-2-hydroxy-1-pyridin-3-ylmethyl-ethyl)-carbamic acid tert-butyl ester. [MH]⁺253.5.

Preparation of ((R)-2-Bromo-1-pyridin-3-ylmethyl-ethyl)-carbamic Acid tert-Butyl Ester To a solution of ((R)-2-hydroxy-1-pyridin-3-ylmethyl-ethyl)-carbamic acid tert-butyl ester (0.43, 1.70 mmol) in dichloromethane (10 ml) is added carbon tetrabromide (0.33 g), 2.04 mmol) and triphenylphosphine (0.23 g, 1.70 mmol). The reaction mixture is stirred at ambient temperature for 2 hours, filtered, and the filtrate partioned between ethylacetate and hydrochloric acid (1M). The aqueous phase is separated, neutralised with saturated sodium bicarbonate solution and extracted into dichloromethane. The dichloromethane is dried over magnesium sulphate and evaporated to afford ((R)-2-bromo-1-pyridin-3-ylmethyl-ethyl)-carbamic acid tert-butyl ester. ¹H NMR (400 MHz, CDCl₃) δ 1.29 (s 9H), 3.05 (dd J 14.3 9.8 1H), 3.18 (dd J 14.3 4.9 1H), 3.51 (d J 4.9 2H) 4.07–4.16 (m 1H) 7.84 (dd J 7.9 5.9 1H), 8.35 (d J 7.9 1H), 8.65 (d, J 5.4 1H), 8.86 (s, 1H).

Preparation of {(R)-2-[4-(4-Fluoro-benzoylypiperidin-1-yl]-1-pyridin-3-ylmethyl-ethyl}-carbamic Acid tert-Butyl Ester (4-Fluoro-phenyl)-piperidin-4-yl-methanone (0.15 g, 0.73 mmol) is added to a solution of ((R)-2-Bromo-1-pyridin-3-ylmethyl-ethyl)-carbamic acid tert-butyl ester (0.21 g, 0.66 mmol) and 1,8 diazabicyclo[5.4.0]undec-7-ene (0.12 ml, 0.79 mmol) in dimethylformamide (3 ml). The reaction mixture is stirred at ambient temperature for 24 hours prior to partioning between ethylacetate and water. The ethylacetate is dried over magnesium sulphate and evaporated. The crude product is purified by flash silica chromatography (97:3 dichloromethane: methanol elution) to afford {(R)-2-[4-(4-fluoro-benzoyl)-piperidin-1-yl]-1-pyridin-3-ylmethyl-ethyl}-carbamic acid tert-butyl ester. ¹H NMR (400 MHz, CDCl₃) δ 1.36 (s, 9H), 1.68–1.85 (br m, 4H), 2.00–2.38 (br m, 4H), 2.78–2.91 (m, 4H), 3.05–3.19 (m 1H), 3.81–3.93 (m 1H) 7.05 (t J 8.8 2H), 7.12–7.18 (m 1H), 7.48 (d J 7.9 1H), 7.85–7.93 (dd J 8.8 5.4 2H), 8.36 (d J 1.5 1H), 8.40 (dd J 4.9 1.5 1H).

Preparation of [1-((R2-Amino-3-pyridin-3-yl-propyl)-piperidin-4-yl]-(4-fluoro-phenyl)-methanone To a solution of {(R)-2-[4-(4-fluoro-benzoyl)-piperidin-1-yl]-1-pyridin-3-ylmethyl-ethyl}-carbamic acid tert-butyl ester (0.149 g, 0.34 mmol) in dichloromethane (2 ml) is added trifluoroacetic acid (0.5 ml) and the reaction mixture stirred at ambient temperature for 1 hour. The reaction mixture is evaporated and the residue takeup in hydrochloric acid (1M), the solution basified with sodium hydroxide solution (4M) and the precipitate extracted into dichloromethane. The dichloromethane was dried over magnesium sulphate and evaporated to afford [1-((R)-2-amino-3-pyridin-3-yl-propyl)-piperidin-4-yl]-(4-fluoro-phenyl)-methanone. ¹H NMR (400 MHz, CDCl₃) δ 1.63–1.85 (m 4H), 1.88–2.00 (m 1H), 2.08–2.32 (m 5H), 2.50 (dd J 13.5 7.9 1H), 2.67 (dd J 13.5 4.9 1H), 2.78–2.98 (m, 2H), 3.04–3.20 (m, 2H), 7.04 (t J 8.8 2H), 7.17 (dd J 6.9 4.9 1H) 7.48 (d J 7.9 1H), 7.88 (dd, J 8.8 5.4 2H), 8.33–8.45 (m, 2H).

Preparation of (E)-3-(3-Cyano-phenyl)-N-{(R)-2-[4-(4-fluoro-benzoyl)-piperidin-1-yl]-1-pyridin-3-ylmethyl-ethyl}-acrylamide To a solution of (E)-3-(4-cyano-phenyl)-acrylic acid (0.022 g, 0.126 mmol) in dichloromethane (1 ml) is added triethylamine (0.016 ml, 0.126 mmol) and (benzotriazo-1-yloxy)tripyrrolidino-phosphonium hexafluorophosphate (0.06 g, 0.116 mmol). The reaction mixture is stirred at ambient temperature for 5 minutes and then a solution of 1-((R)-2-amino-3-pyridin-3-yl-propyl)-piperidin-4-yl]-(4-fluoro-phenyl)-methanone (0.036, 0.105 mmol) in dichloromethane (1 ml) is added. Stirring is continued for a further 1.5 hours, then the reaction mixture is filtered. The filterate is evaporated and the crude product is purified by flash silica chromatography (dichloromethane: methanol: acetic acid, 10:0.5:0.05) to afford (E)-3-(3-cyano-phenyl)-N-{(R)-2-[4-(4-fluoro-benzoyl)-piperidin-1-yl]-1-pyridin-3-ylmethyl-ethyl}-acrylamide. [MH]$^+$497.4.

Method B
Preparation of {(R)-1-Benzyl-2-[4-(4-fluoro-benzoyl)-piperidin-1-yl]-ethyl}-carbamic Acid tert-Butyl Ester A solution of ((R)-1-benzyl-2-oxo-ethyl)-carbamic acid tert-butyl ester (0.5 g, 2.0 mmol), (4-fluoro-phenyl)-piperidin-4-yl-methanone (0.414 g, 2.0 mmol) and sodium triacetoxyborohydride (0.638 g, 3.0 mmol) in tetrahydroftiran (20 ml) is stirred at ambient temperature for 24 hours. The solvent is evaporated and the residue redissolved in dichloromethane and washed with saturated sodium bicarbonate solution. The dichloromethane is dried over magnesium sulphate and evaporated. The crude product is purified by flash silica chromatography (ethylacetate:hexane, 3:1 elution) to afford {(R)-1-benzyl-2-[4-(4-fluoro-benzoyl)-piperidin-1-yl]-ethyl}carbamic acid tert-butyl ester. [MH]$^+$ 441.3.

Preparation of [1-((R-2-Amino-3-phenylpropyl)-piperidin-4-yl]-(4-fluoro-phenyl)-methanone A solution of {(R)-1-benzyl-2-[4-(4-fluoro-benzoyl)-piperidin-1-yl]-ethyl}-carbamic acid tert-butyl ester (1.12 g, 2.54 mmol) and trifluoroacetic acid (3 ml) in dichloromethane (6 ml) is stirred at ambient temperature for 3 hours. The solvent is evaporated and the residue takenup in hydrochloric acid (2M), washed with ethylacetate and basified with sodium hydroxide solution (4M) to pH8–9. The suspension is extracted with dichloromethane, the dichloromethane dried over magnesium sulphate and the solvent evaporated to afford [1-((R)-2-amino-3-phenyl-propyl)-piperidin-4-yl]-(4-fluoro-phenyl)-methanone. [MH]$^+$341.7.

Preparation of (E)-N-{(R)-1-Benzyl-2-[4-(4-fluoro-benzoyl)-piperidin-1-yl]-ethyl}-3(3-cyano-phenyl)-acrylamnide To a solution of (E)-3-(4-cyano-phenyl)-acrylic acid (0.042 g, 0.242 mmol) in dichloromethane (1 ml) is added triethylamine (0.046 ml, 0.331 mmol) and (benzotriazo-1-yloxy)tripyrrolidino-phosphonium hexafluorophosphate (0.126 g, 0.242 mmol). The reaction mixture is stirred at ambient temperature for 5 minutes and then a solution of [1-((R)-2-amino-3-phenyl-propyl)-piperidin-4-yl]-(4-fluoro-phenyl)-methanone (0.075, 0.220 mmol) in dichloromethane (1 ml) is added. Stirring is continued for a further 3 hours, then the reaction mixture is diluted with dichloromethane (25 ml) and washed with saturated sodium bicarbonate solution and saturated brine. The dichloromethane is dried over magnesium sulphate and the solvent evaporated. The crude product is purified by flash silica chromatography (ethyl acetate:hexane, 5:1 elution) to afford (E)-N-{(R)-1-Benzyl-2-[4-(4-fluoro-benzoyl)-piperidin-1-yl]-ethyl}-3-(3-cyano-phenyl)-acrylamide. [MH]$^+$496.8.

Method C
Preparation of (E)-3-(5-Bromo-2-methoxy-phenyl)-N-{2-[4-(4-chloro-benzoyl)-piperidin-1-yl]-ethyl}-acrylamide To a suspension of 2-(formyl-3-methoxyphenoxy)ethyl polystyrene (AMEBA) resin (ex Novabiochem) (6.85 g, 3.33 mmol) in a mixture of methanol/dichloromethane (60 ml, 1:1 v/v) is added 2-amino ethanol and sodium triacetoxyborohydride (4.00 g, 18.85 mmol) and the mixture shaken for 16 hours at 20° C., then filtered. The resin is washed with methanol, DMF and dichloromethane, then dried under vacuum. A THF/acetonitrile mixture (50 ml, 1:1 v/v) is added to the dried resin followed by iodine (4.80 g, 18.85 mmol), imidazole (1.28 g, 18.85 mmol) and triphenylphosphine (4.90 g,18.85 mmol). The suspension obtained is shaken for 18 hours at 20° C., then filtered. The resin is washed with THF and dried under vacuum. To the freshly prepared resin (0.50 g, 0.35 mmol) is added a solution of (4-chloro-phenyl)-piperidin-4-yl-methanone hydrochloride (0.18 g, 0.70 mmol) dissolved in DMF (2 ml) and diisopropylethylamine (0.36 g, 2.8 mmol). The mixture is heated at 50° C. for 16 hours and then filtered. The resin is washed with DMF. To the washed resin are added (E)-3-(5-Bromo-2-methoxy-phenyl)-acrylic acid (0.27 g, 1.05 mmol), 2-(1H benzotriazol-1-yl)-1,1,3,3,-tetramethyluronium tetrafluoroborate (0.34 g, 1.05 mmol), diisopropylethylamine (0.29 g, 1.05 mmol) and DMF (4 ml) and the mixture is shaken at 20° C. for 16 hours, then washed with DMF and methanol, after which it is treated with trifluoroacetic acid/dichloromethane (6 ml, 1:1 v/v) at 20° C. for 1 hour to remove the product from the resin. The resulting mixture is filtered and the filtrate evaporated under vacuum to give the product, [MH]$^+$506.7.

Method D
Preparation of {(R)-1-(4-Amino-benzyl)-2-[4-(4-fluoro-benzoyl)-piperidin-1-yl]-ethyl}-carbamic Acid tert-Butyl Ester To a solution of [(R)-2-[4-(4-fluoro-benzoyl)-piperidin-1-yl]-1-(4-nitro-benzyl)-ethyl]-carbamic acid tert-butyl ester (1.41 g, 2.90 mmol) in acetic acid (11 ml), cooled to 0° C., is added an aqueous solution of calcium chloride (4 ml, 0.47M) and zinc dust (3.9 g, 59.6 mmol). The reaction mixture is stirred at 0° C. for 35 minutes and then filtered through a celite plug. The filtrate is evaporated and the residue dissolved in water and extracted into dichloromethane. The dichloromethane is evaporated and the residue disolved in water and basified with aqueous sodium bicarbonate solution and extracted into dichloromethane. The dichloromethane is dried over magnesium sulphate and evaporated to afford {(R)-1-(4-amino-benzyl)-2-[4-(4-fluoro-benzoyl)-piperidin-1-yl]-ethyl}-carbamic acid tert-butyl ester, [MH]$^+$456.5.

Preparation of [(R)-2-[4-(4-Fluoro-benzoyl)-piperidin-1-yl]-1-(4-methanesulfonylamino-benzyl)-ethyl]-carbamic Acid tert-Butyl Ester To a solution of ((R)-1-(4-amino-benzyl)-2-[4-(4-fluoro-benzoyl)-piperidin-1-yl]-ethyl)-carbamic acid tert-butyl ester (1.19 g, 2.61 mmol) in dichloromethane (15 ml) cooled to 0° C. is added triethylamine (0.37 ml, 2.65 mmol) and methanesulfonylchloride (0.192 ml, 2.49mmol). The reaction mixture is allowed to warm to ambient temperature with stirring for 1 hour, then washed with water and saturated brine solution, dried over magnesium sulphate and evaporated. The crude product is purified by flash silica chromatography (ethylacetate:hexane gradient 6:4 to 1:0 elution) to afford [(R)-2-[4-(4-fluoro-benzoyl)-piperidin-1-yl]-1-(4-methanesulfonylamino-benzyl)-ethyl]-carbamic acid tert-butyl ester. [MH]$^+$534.7.

Method E

Preparation of (S)-4-[4-(4-Chloro-benzoyl)-piperidin-1-ylmethyl]-2,2-dimethyl-oxazolidine-3-carboxylic Acid tert-Butyl Ester

To a solution of (R)4-formyl-2,2-dimethyl-oxazolidine-3-carboxylic acid tert-butyl ester (0.5 g, 2.18 mmol) in tetrahydrofuran (15 ml) is added (4-chloro-phenyl)-piperidin-4-yl-methanone (0.49 g, 2.18 mmol) and sodium triacetoxyborohydride (0.69 g, 3.27 mmol), and the reaction mixture stirred for 3.5 hours at ambient temperature. The solvent is evaporated and the residue partitioned between ethyl acetate (50 ml) and saturated sodium bicarbonate solution (50 ml). The ethyl acetate is dried over magnesium sulphate and evaporated. The crude product is purified by flash silica chromatography (ethyl acetate:hexane, 1:1 elution) to afford (S)-4-[4-(4-chloro-benzoyl)-piperidin-1-ylmethyl]-2,2-dimethyl-oxazoldine-3-carboxylic acid tert-butyl ester, $[MH]^+$ 437.2.

Preparation of [1-((S)-2-Amino-3-hydroxy-propyl)-piperidin-4-yl]- (4-chloro-phenyl)-methanone Hydrochloride

(S)-4-[4-(4-chloro-benzoyl)-piperidin-1-ylmethyl]-2,2-dimethyl-oxazolidine-3-carboxylic acid tert-butyl ester (0.68 g, 1.55 mmol) is added to a solution of hydrogen chloride in ethanol (5 ml, 5.5M). The reaction mixture is stirred at ambient temperature for 1 hour, then evaporated to dryness to afford [1-((S)-2-amino-3-hydroxy-propyl)-piperidin-4-yl]-(4-chloro-phenyl)-methanone hydrochloride. [MH] 297.0.

Preparation of (E)-3-(5-cyano-2-methoxy-phenyl)-acrylic Acid

To a suspension of palladium(II)acetate (0.77 g, 3.42 mmol) in N,N-dimethylacetamide (375 ml) are added tetraethylammonium chloride (19.36 g, 114.5 mmol), dicyclohexyl methyl amine (35.1 g, 174.5 mmol), and 3-bromo-4-methoxybenzonitrile (25.51 g, 118.0 mmol) under a nitrogen atmosphere. The suspension is heated to 100–105° C. whereupon t-butyl acrylate (14.82 g, 114.5 mmol) is slowly added over a period of 45 min. After a further 30–60 min stirring at 100° C., the solution is cooled to room temperature and diluted with TBME (375 ml). The resulting biphasic mixture is stirred vigorously for 10 min. The (upper) TBME phase is successively washed with water (100 ml), 10% aq. citric acid (100 ml) and 25% aq. NaCl (100 ml). The combined aqueous phases are extracted with TBME (100 ml). After adding active charcoal (0.4 g), the combined TBME phases are stirred vigorously for 10 min and filtered. Anhydrous $Na_2SO_4$ (10 g) is added and the resulting suspension is stirred for another 10 min and filtered. The filtrate is concentrated to a volume of 50–70 ml under reduced pressure and, over a period of 25–30 min, added at room temperature to anhydrous trifluoroacetic acid (150 ml). The resulting solution is stirred at room temperature for 60 min (precipitation forms), cooled to 0–5° C. in an ice bath, and diluted with ethyl acetate (410 ml). After stirring vigorously at 0° C. for an additional 60 min, the suspension is filtered. The residue is dried under vacuum at 45–50° C. to give (E)-3-(5-cyano-2-methoxy-phenyl)-acrylic acid as a crystalline solid, mp. 252–253° C. MS (ES): $[M-H]^-$ 202.

Preparation of (E)-N-{(S)-2-[4-(4-Chlorobenzoyl)-piperidin-1-yl]-1-hydroxymethyl-ethyl}-3-(5-cyano-2-methoxy-phenyl)-acrylamide

A solution of (E)-3-(5-cyano-2-methoxy-phenyl)-acrylic acid (0.31 g, 1.55 mmol), triethylamine (0.2 ml, 1.55 mmol) and 2-(1H benzotriazol-1-yl)-1,1,3,3,-tetramethyluronium tetrafluoroborate (0.49 g 1.55 mmol) in dichloromethane (5 ml), is added to a solution of [1-((S)-2-amino-3-hydroxy-propyl)-piperidin-4-yl]-(4-chloro-phenyl)-methanone hydrochloride and triethylamine (0.4 ml, 3.1 mmol) in dichloromethane (5 ml), and the reaction mixture stirred at ambient temperature for 1 hour. The reaction mixture is diluted with dichloromethane (20 ml), washed successively with saturated sodium bicarbonate solution (25 ml) and brine (25 ml), then dried over magnesium sulphate. The solvent is evaporated and the crude residue purified by flash silica chromatography (methanol:dichloromethane; 5:95) to afford (E)-N-{(S)-2-[4-(4-chloro-benzoyl)-piperidin-1-yl]-1-hydroxymethyl-ethyl}-3-(5-cyano-2-methoxy-phenyl)-acrylamide. $[MH]^+$ 482.2.

Method F

Preparation of (S)-4-[4-(4-Fluoro-benzoyl)-piperidin-1-ylmethyl]-2,2-dimethyl-oxazolidine-3-carboxylic Acid tert-Butyl Ester

To a solution of (4-fluoro-phenyl)-piperidin-4-yl-methanone (3.5 g, 17 mmol) in dry tetrahydrofuran (50 ml) is added (R)-4-formyl-2,2-dimethyl-oxazolidine-3-carboxylic acid tert-butyl ester (3.9 g, 17 mmol) and sodium triacetoxyborohydride (5.4 g, 25 mmol), and the reaction mixture stirred for 18 hours at ambient temperature. The reaction mixture is filtered and the solvent evaporated to give a white solid. The solid is taken up in dichloromethane (50 ml) and washed with saturated sodium bicarbonate solution (50 ml), water (2×50 ml) and brine (50 ml). The organic phase is dried over magnesium sulphate and evaporated to afford the product, $[MH]^+$ 420.9.

Preparation of [1-((S)-2-Amino-3-hydroxy-propyl)-piperidin-4-yl]-(4-fluoro-phenyl)-methanone Hydrochloride

To a suspension of (S)-4-[4-(4-fluoro-benzoyl)-piperidin-1-ylmethyl]-2,2-dimethyl-oxazolidne-3-carboxylic acid tert-butyl ester (4.9 g, 11.7 mmol) in ethanol (25 ml) is added hydrogen chloride in dioxane (25 ml, 4M). The resulting clear solution is stirred for 4 hours at ambient temperature during which time a white precipitate forms. The reaction mixture is cooled to 0° C. and the precipitate filtered to afford the product, $[MH]^+$ 281.6.

Preparation of (E)-N-{(S)-2-[4-(4-Fluoro-benzoyl)-piperidin-1-yl]-1-hydroxymethyl-ethyl}-3-(5-cyano-2-methoxy-phenyl)-acrylamide

To a solution of [1-((S)-2-amino-3-hydroxy-propyl)-piperidin-4-yl]-(4-fluoro-phenyl)-methanone hydrochloride (1.8 g, 5.7 mmol) and diisopropylethylamine (2.0 ml, 11.4 mmol) in dichloromethane (45 ml) is added (E)-3-(5-cyano-2-methoxy-phenyl)-acrylic acid (1.1 g, 5.7 mmol) followed by 2-(1H benzotriazol-1-yl)-1,1,3,3,-tetramethyluronium tetrafluoroborate (1.83 g, 5.7 mmol). The reaction mixture is stirred at ambient temperature for 4.5 hours, then filtered and the filtrate washed with water (50 ml), saturated sodium bicarbonate solution (50 ml), water (50 ml) and brine (50 ml). The organic phase is dried over magnesium sulphate, the solvent evaporated and the residue purified by flash silica chromatography (dichloromethane:methanol; 98:2 to 92:8 elution gradient) to afford the product, $[MH]^+$ 466.1.

Method G

Preparation of (S)-4-[4-(4-Chlorobenzoyl)-piperidin-1-ylmethyl]-2,2-dimethyl-oxazolidine-3-carboxylic Acid tert-Butyl Ester Dibenzoyl-L-tartrate (Dibasic)

To a cooled (0° C.) suspension of sodium borohydride (2.40 g, 63.55 mmol) in dry toluene (50 ml) under an inert gas atmosphere acetic acid (11.45 g, 189.9 mmol) is added over a period of 1 hr. Stirring is continued at ambient temperature for 5 hr, until hydrogen evolution has ceased (=Suspension 1). In a separate flask, 4-(4-chlorobenzoyl)-piperidine hydrochloride (obtained by reaction of N-formyl- 4-(4-chlorobenzoyl)-piperidine and acetyl chloride) (5.51 g, 21.18 mmol) is suspended in dry toluene (20 ml) at room temperature. Triethylamine (2.57 g, 25.42 mmol) is added and a toluene solution (55 ml) of (R)-4-formyl-2,2-dimethyl oxazolidine-3-carboxylic acid tert-butyl ester (5.59 g, 24.36 mmol), is added dropwise over a period of 45 min with stirring. Stirring is continued for another 20 min, before Suspension 1 is slowly added with stirring over a period of 60 min. The resulting suspension is stirred at ambient temperature until TLC shows complete consumption of starting material (14 hr), then slowly added to a solution of $NaHCO_3$ (25 g, 297.6 mmol) in water (120 ml). The resulting emulsion is stirred at 20° C. for 60 min, the aqueous phase of the mixture is separated and the organic phase is washed twice successively with 20 ml each of 10% aq. $NaHCO_3$ and water. After adjusting the pH of the combined aqueous phases to 9.5 with solid $Na_2CO_3$, the aqueous phases are extracted with toluene (2×25 ml). Celite (0.5 g) is added to the combined organic phases, which are subsequently filtered and evaporated to dryness to afford the free base, which is taken up in isopropanol (35 ml) and heated to reflux temperature. A solution of di-O,O-benzoyl-L-tartaric acid (4.0 g, 10.6 mmol) in isopropanol (10 ml) is added dropwise. After stirring at 79–81° C. for 20 min, the mixture is cooled, diluted with tert-butyl methyl ether (TBME) and the product crystallised at 0° C., filtered off, washed with a cold (0° C.) 1:2-mixture of TBME-isopropanol (15 ml) and cold (0° C.) TBME (3×5 ml), and dried under vacuum. Recrystallisation of the dried product from isopropanol followed by drying under vacuum gives the title product as a crystalline solid m p 174° C.

MS (ES+): [M]$^+$437.

Preparation of [1-((S)-2-Amino-3-hydroxy-propyl)-piperidin-4-yl]-(4-chloro-phenyl)-methanone Dihydrochloride (S)-4-[4-(4–Chlorobenzoyl)-piperidin-1-ylmethyl]-2,2-dimethyl-oxazolidine-3-carboxylc acid tert-butyl ester dibenzoyl-L-tartrate (dibasic) (4.0 g, 3.2 mmol) is suspended in n-butyl acetate (40 ml). Aqueous (32%) hydrochloric acid (2.18 g, 19.2 mmol) is added and the mixture stirred at ambient temperature until TLC shows complete consumption of starting material (2hr). The suspension is further stirred in an ice bath for 3 hr, and filtered. The solid is washed with cold (0° C.) n-butyl acetate (2×5 ml), and dried under vacuum at 45–50° C. to give the title product as colourless crystals, mp. 232–237° C. MS(ES+): [MH] 297.

Preparation of (E)-3-(5-cyano-2-methoxy-phenyl)-thioacrylic Acid S-benzothiazol-2-yl Ester A suspension of 2,2'-dibenzothiazolyl disulfide (4.0 g, 12.0 mmol) and triphenylphosphine (3.15 g, 12.0 mmol) in $CH_2Cl_2$ (60 ml) is stirred vigorously at 25° C. for 30 min. After cooling to 0° C. in an ice-bath, (E)-3-(5-cyano-2-methoxy-phenyl)-acrylic acid (prepared as described under Method E) (2.24 g, 11.0 mmol) is added, followed by N-methylmorpholine (1.21 ml, 11.0 mmol). The suspension is stirred vigorously and allowed to reach room temperature over night. After stirring a further 24 hr at room temperature, the resulting precipitate is filtered at 0° C. and washed with cold (0° C.) $CH_2Cl_2$ (10 ml). After drying under vacuum at 35° C., the title product is obtained as a crystalline powder, mp. 183–185° C. MS (ES): [M]$^+$352.

Preparation of (E)-N-{(S)-1-[4-(4-Chloro-benzoyl)-piperidin-1-ylmethyl]-2-hydroxy-ethyl}-3-(5-cyano-2-methoxy-phenyl)-acrylamide Hemi-(L)-tartrate To a suspension of [1-((S)-2-amino-3-hydroxy-propyl)-piperidin-4-yl]-(4-chloro-phenyl)-methanone dihydrochloride (9.24 g, 25.0 mmol) in ethanol (250 ml), N-methyl-morpholine is added (2.53 g, 25.0 mmol). The suspension is stirred at 45° C. for 30 min, then (E)-3-(5-cyano-2-methoxy-phenyl)-thioacrylic acid S-benzothiazol-2-yl ester (4.40 g, 12.5 mmol) is added, the suspension diluted with ethanol (20 ml), and stirring at 45° C. is continued for 3 h. More thioester (2.64 g, 7.5 mmol) is added and the suspension is stirred for another 4 h at 45° C. A final portion of thioester (1.76 g, 5.0 mmol) is added and, after stirring for a further 3 hr, more N-methylmorpholine (1.26 g, 12.46 mmol) is added and stirring is continued overnight, before the final addition of N-methylmorpholine (1.26 g, 12.46 mmol). The suspension is filtered immediately and the filtrate taken to dryness under reduced pressure. The residue is taken up in $CH_2Cl_2$ (250 ml) and washed successively with 10% aq. $Na_2CO_3$ (2×100 ml) and 10% aq. NaCl (4×100 ml). The organic phase is stirred with Celite (1 g), filtered, and evaporated to dryness. The residue is dried under vacuum and taken up in ethanol (130 ml). At 35° C., a solution of L-tartaric acid (4.5 g, 30.0 mmol) in ethanol (100 ml) is added under stirring and the resulting suspension is stirred at 50–55° C. until a clear solution has formed. When a crystalline turbidity forms, the suspension is slowly cooled to 0° C. and stirred in an ice bath for another 45 min, before the precipitate is filtered off, washed with cold (0° C.) ethanol (20 ml), and recrystallised from ethanol to give the title product, mp. 90–120° C. (decomp.). MS (ES+): [MH]$^+$482.

Preparation of (E)-N-{(S)-1-[4-(4-Chloro-benzoyl)-piperidin-1-ylmethyl]-2-hydroxy-ethyl}-3-(5-cyano-2-methoxy-phenyl)-acrylamide 10% aq. $Na_2CO_3$ (100 ml) is added, with stirring, at room temperature to a suspension of (E)-N-{(S)-1-[4-(4-chloro-benzoyl)-piperidin-1-ylmethyl]-2-hydroxy-ethyl}-3-(5-cyano-2-methoxy-phenyl)-acrylamide hemi-(L)-tartrate (6.32 g, 10.0 mmol) in $CH_2Cl_2$ (150 ml) and water (50 ml). After stirring at ambient temperature for 30 min, the phases are separated and the aqueous phase is extracted with $CH_2Cl_2$ (100 ml). The combined $CH_2Cl_2$ phases are extracted with 10% aq. NaCl (2×100 ml), stirred with Celite (500 mg) and filtered to give, after evaporation under reduced pressure, a colourless foam. After addition of butyl acetate (200 ml), a clear solution forms, which is warmed to 80° C. and allowed to cool slowly to room temperature. After dilution with TBME (150 ml), the suspension is cooled to 0° C., the precipitated crystals are filtered off, washed with a cold (0° C.) 1:1-mixture of butyl acetate/TBME (50 ml) and dried under vacuum at 45–50° C. to give (E)-N-((S)-1-[4-(4–Chloro-benzoyl)-piperidin-1-ylmethyl]-2-hydroxy-ethyl}-3-(5-cyano-2-methoxy-phenyl)-acrylamide. Mp. 162–163° C. MS (EI+): [MH]$^+$482.

What is claimed is:

1. A compound of formula

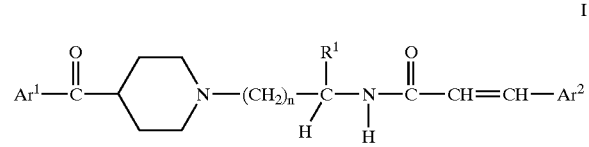

I in free or salt form, where
- $Ar^1$ is phenyl substituted by one or more halogen atoms,
- $Ar^2$ is phenyl or naphthyl which is unsubstituted or substituted by one or more substituents selected from halogen, cyano, hydroxy, nitro, $C_1$–$C_8$-alkyl, $C_1$–$C_8$-haloalkyl, $C_1$–$C_8$-alkoxy or $C_1$–$C_8$-alkoxycarbonyl,
- $R^1$ is hydrogen or $C_1$–$C_8$-alkyl optionally substituted by hydroxy, $C_1$–$C_8$-alkoxy, acyloxy, $N(R^2)R^3$, halogen, carboxy, $C_1$–$C_8$-alkoxycarbonyl, —CON($R^4$)$R^5$ or by a monovalent cyclic organic group, $R^2$ and $R^3$ are each independently hydrogen or $C_1$–$C_8$-alkyl, or $R^2$ is hydrogen and $R^3$ is acyl or —$SO_2R^6$, or $R^2$ and $R^3$ together with the nitrogen atom to which they are attached denote a 5- or 6-membered heterocyclic group, $R^4$ and $R^5$ are each independently hydrogen or $C_1$–$C_8$-alkyl, or $R^4$ and $R^5$ together with the nitrogen atom to which they are attached denote a 5- or 6-membered heterocyclic group, $R^6$ is $C_1$–$C_8$-alkyl, $C_1$–$C_8$-haloalkyl, or phenyl optionally substituted by $C_1$–$C_8$-alkyl, and n is 1, 2,3 or 4, with the proviso that when $Ar^1$ is p-chlorophenyl and $R^1$ is hydrogen, $Ar^2$ is not phenyl or p-nitrophenyl.

2. A compound according to claim 1, in which $Ar^2$ is monosubstituted phenyl in which the substituent is halogen, cyano, nitro or $C_1$–$C_4$-alkoxy; or disubstituted phenyl in which the substituents are selected from halogen, cyano, hydroxy, nitro, $C_1$–$C_4$-alkoxy, $C_1$–$C_4$-alkyl and $C_1$–$C_4$-haloalkyl; or trisubstituted phenyl in which the substituents are selected from halogen, hydroxy, $C_1$–$C_4$-alkoxy and $C_1$–$C_4$-alkoxycarbonyl; or penta-substituted phenyl in which the substituents are halogen.

3. A compound according to claim 1, in which R1 is $C_1$–$C_4$-alkyl optionally substituted by hydroxy, $C_1$–$C_8$-alkoxy, acyloxy, halogen, carboxy, $C_1$–$C_8$-alkoxycarbonyl, —CON($R^4$)$R^5$ or by a monovalent cyclic organic group.

4. A compound according to claim 1, in which $Ar^1$ is phenyl substituted by fluorine or chlorine para to the indicated carbonyl group and optionally further substituted by halogen ortho to the indicated carbonyl group, $Ar^2$ is phenyl monosubstituted by a substituent selected from halogen, cyano, nitro and $C_1$–$C_4$-alkoxy, phenyl substituted by two substituents, which may be the same or different, selected from halogen, cyano, hydroxy, $C_1$–$C_4$-alkoxy, $C_1$–$C_4$-alkyl, $C_1$–$C_4$-haloalkyl and nitro, or phenyl substituted by three substituents, which may be the same or different, selected from halogen, hydroxy, $C_1$–$C_4$-alkoxy and $C_1$–$C_4$-alkoxycarbonyl, $R^1$ is hydrogen, $C_1$–$C_4$-alkyl or $C_1$–$C_4$-alkyl substituted by hydroxy, $C_3$–$C_8$-cycloalkyl, phenyl, $C_1$–$C_4$-alkylsufonylamino-substiruted phenyl or a 5- or 6-membered heterocyclic aromatic group having one or more ring hetero atoms selected from nitrogen, oxygen and sulfur, and n is 1 or 2.

5. A compound according to claim 1, in which $Ar^1$ is phenyl substituted by fluorine or chlorine para to the indicated carbonyl group, $Ar^2$ is phenyl substituted ortho to the indicated —CH=CH— group by $C_1$–$C_4$-alkoxy and para to the $C_1$–$C_4$-alkoxy group by cyano, halogen or $C_1$–$C_4$-alkoxy, $R^1$ is $C_1$–$C_4$-alkyl substituted by hydroxy, phenyl, $C_1$–$C_4$-alkylsulfonylamino-substituted phenyl or a 5- or 6-membered heterocyclic aromatic group having one or two ring hetero atoms selected from nitrogen, oxygen and sulfur, and n is 1.

6. A compound of formula

XI

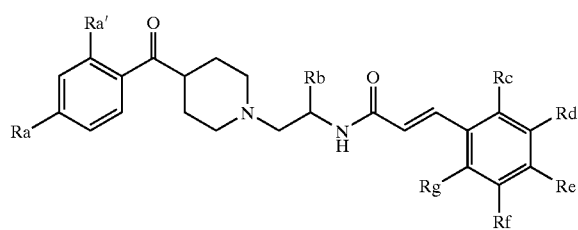

in free or salt form, where Ra' is hydrogen and Ra, Rb, Rc, Rd, Re, Rf, and Rg are as defined in the following table

| Ra | Rb | Rc | Rd | Re | Rf | Rg |
|----|----|----|----|----|----|----|
| F | H | H | CN | H | H | H |
| F | 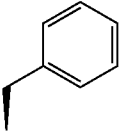 | H | CN | H | H | H |
| F | 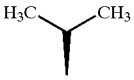 H₃C  CH₃ | H | CN | H | H | H |
| F | 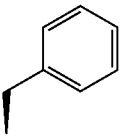 | OCH₂CH₃ | H | H | Br | H |
| F | H | H | CN | OCH₃ | H | H |
| F | H | OCH₃ | H | H | OCH₃ | H |
| F | H | OCH₃ | H | H | Br | H |

-continued
| Ra | Rb | Rc | Rd | Re | Rf | Rg |
|---|---|---|---|---|---|---|
| F | 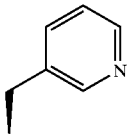 | H | CN | H | H | H |
| F | 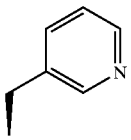 | OCH₃ | H | H | Br | H |
| F | H | OH | H | H | Cl | H |
| F | H | OCH₃ | H | H | F | H |
| Cl | H | OCH₃ | H | H | Br | H |
| F | H | OCH₃ | H | H | CN | H |
| F | H | OCH₃ | H | H | Cl | H |
| F | H | OCH₂CH₃ | H | H | Cl | H |
| F | H | O(CH₂)₂CH₃ | H | H | Cl | H |
| F | H |  | H | H | Cl | H |
| F | H | O(CH₂)₂CH₃ | H | H | Br | H |
| F | H |  | H | H | Br | H |
| F | H | OCH₃ | H | H | CH₃ | H |
| F | H |  | H | H | CH₃ | H |
| F | 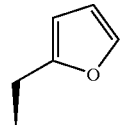 | H | H | H | CN | H |
| F | 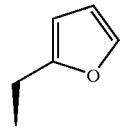 | OCH₃ | H | H | OCH₃ | H |
| F |  | OCH₃ | H | H | Br | H |
| F | 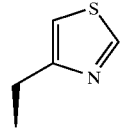 | H | H | H | CN | H |

-continued

| Ra | Rb | Rc | Rd | Re | Rf | Rg |
|---|---|---|---|---|---|---|
| F | 4-(methylsulfonamido)benzyl | OCH$_3$ | H | H | OCH$_3$ | H |
| F | furan-2-ylmethyl | OCH$_3$ | H | H | CN | H |
| F | furan-2-ylmethyl | OCH$_3$ | H | H | Br | H |
| F | 1H-imidazol-4-ylmethyl | OCH$_3$ | H | H | CN | H |
| F | furan-2-ylmethyl (racemic) | OCH$_3$ | H | H | CN | H |
| F | H | H | H | CH$_3$ | H | H |
| F | H | F | F | F | F | F |
| F | H | H | CF$_3$ | H | CF$_3$ | H |
| F | H | H | NO$_2$ | H | H | H |
| F | H | H | COOCH$_3$ | OCH$_3$ | H | OCH$_3$ |
| F | CH$_2$OH | OCH$_3$ | H | H | CN | H |
| Cl | CH$_2$OH | OCH$_3$ | H | H | CN | H |
| F | CH$_3$ | H | H | H | CN | H |
| Cl | CH$_2$OH | OCH$_3$ | H | H | Cl | H |
| Cl | H | OCH$_3$ | H | H | CN | H |
| F | CH$_2$CH$_2$OH | OCH$_3$ | H | H | Br | H |
| Cl | CH$_2$OH | OCH$_3$ | H | H | Br | H |

-continued

| Ra | Rb | Rc | Rd | Re | Rf | Rg |
|---|---|---|---|---|---|---|
| F | 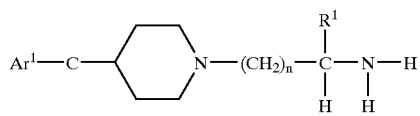 | OCH$_3$ | H | H | CN | H |
| F | 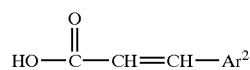 | OCH$_3$ | H | H | CN | H | or where Ra and Ra' are fluorine, Rb, Rd, Re and Rg are hydrogen, Rc is methoxy and Rf is bromine.

7. A compound according to claim 1 in combination with an anti-inflammatory, bronchodilatory or antihistamine drug substance.

8. A pharmaceutical composition comprising as active ingredient a compound according to claim 1, optionally together with a pharmaceutical acceptable diluent or carrier therefor.

9. A process for the preparation of compounds of formula I according to claim 1 which comprises
   (i) (A) reacting a compound of formula

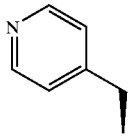

II with a compound of formula

III or an amide-forming derivative thereof, where Ar$^1$, Ar$^2$, R$^1$ and n are as hereinbefore defined, or (B) reacting a compound of formula III, or an amide forming derivative thereof, with a compound of formula

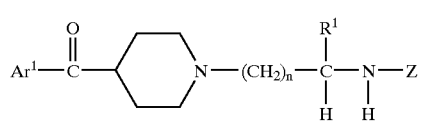

IV where Ar$^1$, R$^1$ and n are as hereinbefore defined and Z denotes a solid phase substrate chemically linked to the indicated nitrogen atom, and detaching the resulting product from the substrate to replace Z by hydrogen; and
   (ii) recovering the product in free or salt form.

10. A compound according to claim 4 in combination with an anti-inflammatory, bronchodilatory or antihistamine drug substance.

11. A compound according to claim 6 in combination with an anti-inflammatory, bronchodilatory or antihistamine drug substance.

12. A pharmaceutical composition comprising as active ingredient a compound according to claim 4, optionally together with a pharmaceutically acceptable diluent or carrier therefor.

13. A pharmaceutical composition comprising as active ingredient a compound according to claim 6, optionally together with a pharmaceutically acceptable diluent or carrier therefor.

14. A method of treating a condition mediated by CCR-3 in a subject in need of such treatment, which comprises administering to said subject an effective amount of a compound of formula I as defined in claim 1 in free form or in the form of a pharmaceutically acceptable salt.

15. A method of treating a condition mediated by CCR-3 in a subject in need of such treatment, which comprises administering to said subject an effective amount of a compound of formula I as defined in claim 4 in free form or in the form of a pharmaceutically acceptable salt.

16. A method of treating a condition mediated by CCR-3 in a subject in need of such treatment, which comprises administering to said subject an effective amount of a compound of formulas XI as defined in claim 6 in free form or in the form of a pharmaceutically acceptable salt.

17. A method according to claim 14 wherein the condition is an inflammatory or allergic condition.

18. A method according to claim 17 wherein the inflammatory or allergic condition is an inflammatory or obstructive airways disease.

19. A method according to claim 14 wherein the condition is a condition or disease of the eye.

20. A method according to claim 19 wherein the condition or disease of the eye is conjunctivitis, keratoconjunctivitis sicca or vernal conjunctivitis.

* * * * *

UNITED STATES PATENT AND TRADEMARK OFFICE
CERTIFICATE OF CORRECTION

PATENT NO. : 6,670,379 B2
DATED : December 30, 2003
INVENTOR(S) : Howe et al.

Page 1 of 1

It is certified that error appears in the above-identified patent and that said Letters Patent is hereby corrected as shown below:

Title page,
Item [57], ABSTRACT, the chemical formulae should read as follows:

Column 2,
Line 56, the chemical formulae should read as follows:

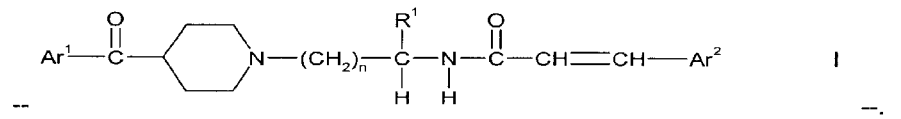

Column 28,
Lines 38, should read as follows:
-- Rd, Re, Rf, and Rg are as defined in the following table --.

Column 33,
Line 32, the chamical formulae should read as follows:

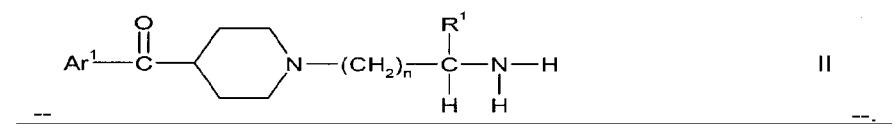

Signed and Sealed this

Twentieth Day of July, 2004

JON W. DUDAS
*Acting Director of the United States Patent and Trademark Office*